US00RE43834E

(19) United States
(12) Reissued Patent
Steenfeldt-Jensen et al.

(10) Patent Number: US RE43,834 E
(45) **Date of Reissued Patent: *Nov. 27, 2012**

(54) INJECTION SYRINGE

(75) Inventors: Soren Steenfeldt-Jensen, Hornback (DK); Steffen Hansen, Hillerod (DK)

(73) Assignee: Novo Nordisk A/S, Bagsvaerd (DK)

( * ) Notice: This patent is subject to a terminal disclaimer.

(21) Appl. No.: 10/442,855

(22) Filed: May 21, 2003

Related U.S. Patent Documents

Reissue of:
(64) Patent No.: 6,235,004
Issued: May 22, 2001
Appl. No.: 09/429,677
Filed: Oct. 28, 1999

U.S. Applications:
(63) Continuation of application No. 09/238,849, filed on Jan. 28, 1999, now Pat. No. 6,004,297.

(60) Provisional application No. 60/073,820, filed on Feb. 5, 1998.

(30) Foreign Application Priority Data

Jan. 20, 1998 (DK) ..... 1998 00130

(51) Int. Cl.
*A61M 5/00* (2006.01)

(52) U.S. Cl. ..... 604/207; 604/211

(58) Field of Classification Search ..... 604/207–211, 604/187, 218, 232
See application file for complete search history.

(56) References Cited

U.S. PATENT DOCUMENTS

| | | | | |
|---|---|---|---|---|
| 2,444,570 | A | 8/1946 | Lawrence et al. | |
| 4,470,317 | A | 9/1984 | Sabloewski et al. | |
| 4,498,904 | A | 2/1985 | Turner et al. | |
| 4,568,335 | A | 2/1986 | Updike et al. | |
| 4,585,439 | A | 4/1986 | Michel | |
| 4,592,745 | A * | 6/1986 | Rex et al. | 604/211 |
| 4,833,379 | A | 5/1989 | Kaibel et al. | |
| 4,865,591 | A | 9/1989 | Sams | |
| 4,883,472 | A | 11/1989 | Michel | |
| 4,919,596 | A | 4/1990 | Slate et al. | |
| 4,936,833 | A | 6/1990 | Sams | |
| 4,973,318 | A | 11/1990 | Holm | |
| 4,994,033 | A | 2/1991 | Shockey et al. | |
| 5,017,190 | A * | 5/1991 | Simon et al. | 604/207 |

(Continued)

FOREIGN PATENT DOCUMENTS

DE SO 3609555 9/1987

(Continued)

OTHER PUBLICATIONS

U.S. Appl. No. 10/442,855, filed May 21, 2003, Steenfeldt-Jensen.

(Continued)

*Primary Examiner* — Manuel A Mendez
(74) *Attorney, Agent, or Firm* — Marc A. Began

(57) ABSTRACT

The present invention provides an injection syringe comprises a housing including a holder for containing a cartridge of medicine, a piston rod with a non-circular cross-section having an outer thread, a piston rod drive, a one way coupling having an annular ring of internal ratchet notches, which annular ring can be integral with the housing, and a pawl having at least a pair of resilient arms each having a free end.

48 Claims, 5 Drawing Sheets

Figure 1:
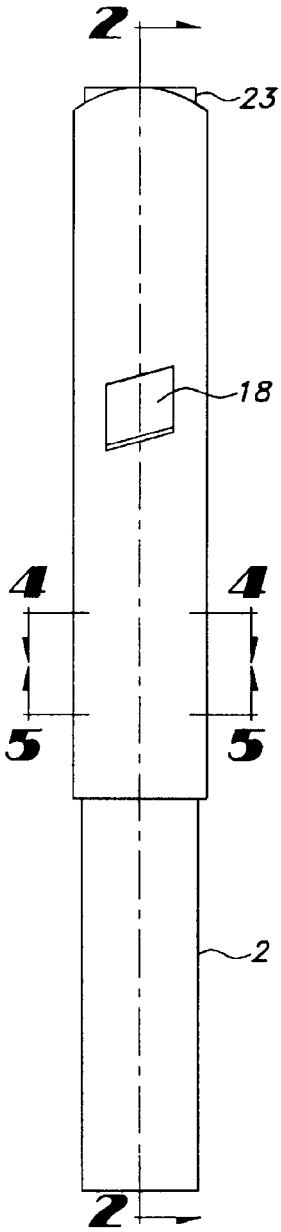

U.S. PATENT DOCUMENTS 5,112,317 A 5/1992 Michel
5,207,752 A 5/1993 Sorenson et al.
5,226,895 A 7/1993 Harris
5,246,417 A 9/1993 Haak et al.
5,257,987 A 11/1993 Athayde et al.
5,271,527 A 12/1993 Haber et al.
5,279,585 A 1/1994 Balkwill
5,279,586 A 1/1994 Balkwill
5,281,198 A 1/1994 Haber et al.
5,284,480 A 2/1994 Porter et al.
5,304,152 A * 4/1994 Sams ..... 604/207
5,308,340 A * 5/1994 Harris ..... 604/208
5,314,412 A 5/1994 Rex
5,318,540 A 6/1994 Athayde et al.
5,320,609 A 6/1994 Haber et al.
5,331,954 A 7/1994 Rex et al.
5,370,629 A 12/1994 Michel et al.
5,380,297 A 1/1995 Wadman et al.
5,383,865 A 1/1995 Michel
5,440,976 A 8/1995 Giuliano et al.
5,445,606 A 8/1995 Haak et al.
5,447,150 A 9/1995 Bacon
5,478,316 A 12/1995 Bitdinger et al.
5,480,387 A 1/1996 Gabriel et al.
5,492,534 A 2/1996 Athayde et al.
5,505,704 A 4/1996 Pawelka et al.
5,545,147 A 8/1996 Harris
5,546,932 A 8/1996 Galli
5,549,574 A 8/1996 Townsend
5,549,575 A 8/1996 Giambattista
5,584,815 A 12/1996 Pawelka et al.
5,591,136 A 1/1997 Gabriel
5,599,314 A * 2/1997 Neill ..... 604/207
5,611,783 A 3/1997 Mikkelson
5,626,566 A * 5/1997 Petersen et al. ..... 604/208
5,645,052 A 7/1997 Kersey
5,674,204 A * 10/1997 Chanoch ..... 604/211
5,679,111 A * 10/1997 Hjertman et al. ..... 604/135
5,681,285 A 10/1997 Ford et al.
5,685,864 A 11/1997 Shanley et al.
5,688,251 A 11/1997 Chanoch
5,693,027 A 12/1997 Hansen et al.
5,709,662 A 1/1998 Olive et al.
5,716,990 A 2/1998 Bagshawe et al.
5,725,508 A * 3/1998 Chanoch et al. ..... 604/207
5,743,889 A 4/1998 Sams
5,755,692 A 5/1998 Manicom
5,823,998 A 10/1998 Yamagata
5,827,232 A 10/1998 Chanoch
5,843,036 A 12/1998 Olive et al.
5,882,718 A 3/1999 Pommer et al.
5,898,028 A 4/1999 Jensen et al.
5,921,966 A 7/1999 Bendek et al.
5,928,201 A 7/1999 Poulsen et al.
5,938,642 A 8/1999 Burroughs et al.
5,947,934 A 9/1999 Hanjen et al.
5,951,530 A 9/1999 Steengaard et al.
5,954,689 A 9/1999 Poulsen
5,961,496 A 10/1999 Nielsen et al.
5,980,491 A 11/1999 Hansen
5,984,900 A 11/1999 Mikkelsen
6,003,736 A 12/1999 Ljunggren
6,004,297 A * 12/1999 Steenfeldt-Jensen et al. ..... 604/211
6,010,485 A 1/2000 Buch-Rasmussen et al.
6,033,376 A 3/2000 Rockley
6,033,377 A 3/2000 Rasmussen et al.
6,048,336 A 4/2000 Gabriel
6,074,372 A 6/2000 Hansen
6,083,197 A 7/2000 Umbaugh
6,086,567 A 7/2000 Kirchhofer et al.
6,096,010 A 8/2000 Walters
6,110,149 A 8/2000 Klitgaard et al.
6,129,080 A 10/2000 Pitcher et al.
6,146,361 A 11/2000 DiBiasi et al.
6,193,698 B1 2/2001 Kirchhofer et al.
6,221,046 B1 4/2001 Burroughs
6,221,053 B1 4/2001 Walters et al.
6,231,540 B1 5/2001 Smedegaard
6,235,004 B1 5/2001 Steenfeldt-Jensen et al.
6,248,090 B1 6/2001 Jensen et al.
6,248,095 B1 6/2001 Giambattista et al.
6,258,062 B1 7/2001 Thielen et al.
6,269,340 B1 7/2001 Ford et al.
6,277,097 B1 8/2001 Mikkelsen et al.
6,277,098 B1 8/2001 Klitmose et al.
6,281,225 B1 8/2001 Hearst et al.
6,283,941 B1 9/2001 Schoenfeld et al.
6,287,283 B1 9/2001 Ljunggreen
6,302,869 B1 10/2001 Klitgaard
6,312,413 B1 11/2001 Jensen et al.
6,340,357 B1 1/2002 Poulsen et al.
6,379,339 B1 4/2002 Klitgaard et al.
6,514,230 B1 2/2003 Munk et al.
6,547,763 B2 4/2003 Steenfeldt-Jensen et al.
6,547,764 B2 4/2003 Larsen et al.
6,562,011 B1 5/2003 Buch-Rasmussen et al.
6,569,126 B1 5/2003 Poulsen et al.
6,582,404 B1 6/2003 Klitgaare et al.
6,605,067 B1 8/2003 Larsen
6,613,019 B2 9/2003 Munk
6,663,602 B2 12/2003 Moller
6,692,472 B2 2/2004 Hansen et al.
6,716,198 B2 4/2004 Larsen
6,726,661 B2 4/2004 Munk et al.
6,770,288 B2 8/2004 Duirs
6,796,970 B1 9/2004 Klitmose et al.
6,893,415 B2 5/2005 Madsen et al.
6,899,698 B2 5/2005 Sams
6,899,699 B2 5/2005 Enggaard
6,945,961 B2 9/2005 Miller et al.
7,008,399 B2 3/2006 Larsen et al.
7,090,662 B2 8/2006 Wimpenny et al.
7,094,221 B2 8/2006 Veasey et al.
7,104,972 B2 9/2006 Moller et al.
7,133,329 B2 11/2006 Skyggebjerg et al.
7,175,055 B2 2/2007 Hansen et al.
2002/0007154 A1 1/2002 Hansen et al.
2002/0052578 A1 5/2002 Moller
2002/0077852 A1 6/2002 Ford et al.
2002/0120235 A1 8/2002 Enggaard
2003/0039679 A1 2/2003 Duirs
2003/0172924 A1 9/2003 Staniforth et al.
2004/0059299 A1 3/2004 Moller
2004/0186431 A1 9/2004 Graf et al.
2004/0210199 A1 10/2004 Atterbury et al.
2004/0236282 A1 11/2004 Braithwaite
2004/0249348 A1 12/2004 Wimpenny et al.
2004/0260247 A1 12/2004 Veasey et al.
2004/0267207 A1 12/2004 Veasey et al.
2005/0004529 A1 1/2005 Veasey et al.
2005/0019400 A1 1/2005 Deveney et al.
2005/0033244 A1 2/2005 Veasey et al.
2005/0055011 A1 3/2005 Engganrd
2005/0205083 A1 9/2005 Staniforth et al.
2005/0268915 A1 12/2005 Wassenaar et al.
2007/0093761 A1 4/2007 Veasey

FOREIGN PATENT DOCUMENTS

EP 295075 12/1988
EP 0 327 910 8/1989
EP 0327910 * 8/1989
EP 327910 8/1989
EP 359070 9/1989
EP 0 450 905 10/1991
EP 0450905 * 10/1991
EP 450905 10/1991
EP 498737 8/1992
EP 554996 8/1993
EP 608343 3/1994
EP 594349 4/1994
EP 0 673 482 9/1995
EP 702970 3/1996
EP 879610 11/1998
EP 0 937 471 2/1999
EP 0 937 476 8/1999

| | | | |
|---|---|---|---|
| EP | 1250167 | B1 | 7/2005 |
| EP | 1570876 | A2 | 7/2005 |
| FR | 2583291 | | 12/1986 |
| FR | 2767479 | | 2/1999 |
| GB | 735443 | | 9/1953 |
| GB | 1232899 | | 5/1971 |
| GB | 2141799 | | 1/1985 |
| JP | 5-337179 | | 12/1993 |
| JP | 05337179 | A | 12/1993 |
| JP | 6-296691 | | 10/1994 |
| JP | 06296691 | A | 10/1994 |
| RU | 2111019 | | 5/1997 |
| WO | WO 89/07463 | | 8/1989 |
| WO | 91/14467 | | 3/1990 |
| WO | 90/09202 | | 8/1990 |
| WO | 91/10460 | | 7/1991 |
| WO | 91/14467 | | 10/1991 |
| WO | 93/07922 | | 4/1993 |
| WO | WO 93/07922 | * | 4/1993 |
| WO | 94/19034 | | 9/1994 |
| WO | 96/26754 | | 9/1996 |
| WO | WO 96/26754 | | 9/1996 |
| WO | WO96/26754 | | 9/1996 |
| WO | WO 96/38190 | | 12/1996 |
| WO | WO 97/36626 | | 10/1997 |
| WO | WO 98/10813 | | 3/1998 |
| WO | WO 98/56436 | | 12/1998 |
| WO | WO 98/57688 | | 12/1998 |
| WO | 99/16487 | | 4/1999 |
| WO | 99/38554 | | 8/1999 |
| WO | WO 99/38554 | | 8/1999 |
| WO | WO 01/19434 | | 3/2001 |

OTHER PUBLICATIONS

U.S. Appl. No. 10/960,900, filed Oct. 7, 2004, Steenfeldt-Jensen.

U.S. Appl. No. 11/121,331, filed May 3, 2005, Steenfeldt-Jensen.

U.S. Appl. No. 11/640,610, filed Dec. 18, 2006, Steenfeldt-Jensen.

May 17, 2002 Office Action in 09768760 and Accompanying 892 and 1149 Forms.

Pair Print-Out of File History of U.S. Appl. No. 10/610,926, Jul. 1, 2003.

Pair Print-Out of File History of U.S. Appl. No. 10/960,900, Oct. 7, 2004.

Pair Print-Out of File History of U.S. Appl. No. 11/121,331, May 30, 2005.

Pair Print-Out of File History of U.S. Appl. No. 11/640,610, Dec. 18, 2006.

Dec. 18, 2008 Office Action in U.S. Appl. No. 10/960,900.

*Novo Nordisk A/S* v. *Sanofi-Aventis U.S. LLC* Amended Complaint filed Oct. 1, 2007 (No. 3:07-cv-03206-MLC-JJH).

*Novo Nordisk A/S* v, *Sanofi-Aventis U.S. LLC* Counter-Claims, Answer, and Affirmative Defense filed Oct. 16, 2007 (No. 3:07-cv-03206-MLC-JJH).

*Novo Nordisk A/S* v. *Sanofi-Aventis U.S. LLC* Affidavit of Charles E. Clemens Filed Sep. 10, 2007 (No. 3:07-cv-03206-MLC-JJH).

*Novo Nordisk A/S* v. *Sanofi-Aventis U.S. LLC* Reply Affidavit of Charles E. Clemens Filed Jan. 31, 2008 (No. 3:07-cv-03206-MLC-JJH).

*Novo Nordisk A/S* v. *Sanofi-Aventis U.S. LLC* Memorandum Opinion Filed Feb. 19, 2008 (No. 3:07-cv-03206-MLC-JJH).

*Novo Nordisk A/S* v. *Sanofi-Aventis U.S. LLC* Declaration of Bernard Sams Filed Feb. 4, 2008 (No. 3:07-cv-03206-MLC-JJH).

*Novo Nordisk A/S* v. *Sanofi-Aventis U.S. LLC* Expert Declaration of Neil Sheehan Filed Jan. 14, 2008 (No. 3:07-cv-03206-MLC-JJH).

*Novo Nordisk A/S* v. *Sanofi-Aventis U.S. LLC* 2$^{nd}$ Expert Declaration of Neil Sheehan Filed Nov. 3, 2008 (No. 3:07-cv-03206-MLC-JJH).

US Office Action Sent Dec. 18, 2008 in Counterpart U.S. Appl. No. 10/960,900.

US Office Action Sent Apr. 17, 2009 in Counterpart U.S. Appl. No. 11/121,331.

US Office Action Sent Apr. 17, 2009 in Counterpart U.S. Appl. No. 11/640,610.

* cited by examiner

INJECTION SYRINGE

Matter enclosed in heavy brackets [ ] appears in the original patent but forms no part of this reissue specification; matter printed in italics indicates the additions made by reissue.

CROSS-REFERENCE TO RELATED APPLICATIONS

[This application is a continuation of U.S. application ser. No. 09/238,849 filed Jan. 28, 1999 now U.S. Pat. 6,004,297, which claims priority under 35 U.S.C. 119 of Danish application PA 1998 00130 filed Jan. 30, 1998 and of U.S. provisional application No. 60/073,820 filed Feb. 5, 1998, the contents of which are fully incorporated herein by reference.] *This application is a reissue of U.S. Pat. No. 6,235,004, issued May 22, 2001 (U.S. application Ser. No. 09/429,677, filed Oct. 28, 1999) which is a continuation of U.S. application Ser. No. 09/238,849, filed Jan. 28, 1999 (U.S. Pat. No. 6,004,297), which claims priority under 35 U.S.C. 119 of Danish Patent Application PA 1998 00130, filed Jan. 30, 1998 and of U.S. Provisional Application 60/073,820, filed Feb. 5, 1998, the contents of which are fully incorporated herein by reference, and is the parent application of U.S. application Ser. No. 11/640,610, filed Dec. 18, 2006 (Abandoned). Additionally, U.S. application Ser. No. 10/960,900, filed Oct. 7, 2004 (Expressly Abandoned) and U.S. application Ser. No. 11/121,331, filed May 3, 2005 (Abandoned) are reissues of U.S. Pat. No. 6,235,004, issued May 22, 2001 (U.S. application Ser. No. 09/429,677, filed Oct. 28, 1999).*

The invention relates to injection syringes of the kind apportioning set doses of a medicine from a cartridge containing an amount of medicine sufficient for the preparation of a number of therapeutic doses.

Such syringes are mainly made for users who have to inject themselves frequently, e. g. diabetics. A number of demands are set to such syringes. The setting of a dose must be easy an unambiguous and it must be easy to read the set dose. It must be possible with a minimum of trouble to cancel or change a wrongly set dose and when the dose is injected the dose setting must return to zero. When a disposable syringe is in question, i.e. a syringe which is disposed of when the cartridge is empty, the syringe must further be cheap and made of materials suited for recycling or burning without producing noxious gases. For these purposes the number of parts from which the syringe is constructed and the number of different kinds of materials used in the syringe should be kept at a minimum.

Most dose setting devices work with a threaded piston rod co-operating with a nut where the nut and the piston rod may be rotated relative to each other. The dose setting may be obtained by screwing the nut away from a stop to which it is returned during the injection by pressing the piston rod until the nut member abuts the stop. By other dose setting devices one of the elements, the nut or the piston rod, is kept inrotatable and the other is allowed to rotate a set angle depending on the set dose, whereby the piston rod is screwed a distance through the nut.

In most syringes for apportioning set doses it is preferred that the piston rod is backing up the piston upon which it works during the injection. To obtain this precaution is taken to prevent the piston rod from moving in a proximal direction.

The syringe according to EP 327 910 is of the type wherein a nut is screwed away from a stop. During the setting of the dose the screwing may be performed in both direction so that a too large set dose may be lowered just by rotating the nut in an opposite direction. Means are provided preventing that negative doses are set. The mutual rotation of the piston rod and the nut is obtained by rotating a cap relative to the pen housing and a set dose may be read on a scale and a pointer provided at adjacent edges of the housing and the cap, these edges being so shaped that the cap can only be mounted firmly on the housing when the pointer points zero on the scale. It may be seen as a weak point that doses larger than the one obtained by rotating the parts 360° must be calculated by adding the number pointed at on the scale and a number printed on the side of a tubular extension of the nut which is moved out from the proximal end of the housing proportionally with the dose set and which tubular extension is closed at its proximal end to form an injection button.

In EP 450 905 the above drawback is overcome by writing the numbers along a helical line on a tubular extension of the nut so that these number may successively be seen in a window in a housing element enclosing said tubular extension. Hereby the size of the dose is indicated unambiguously but the user have to remember to set the dose setting device on zero before the next setting of a dose is performed. If this is forgotten a wrong dose may be set and the number may not be seen clearly in the window.

In EP 608 343 is described a pen having a dose setting mechanism wherein the dose is set by rotating a button relative to a housing to set a dose. By the rotation the button is screwed up from the end of the housing in a thread having a pitch so large that the thread connection is not self blocking, i. e. when the button is presses back to the end of the housing it will rotate back in the thread. The button is through a ratchet coupled to a driver, the ratchet forming a unidirectional coupling which during the rotation of the button in one direction to set a dose rides or clicks over the teeth of the ratchet. The cylindrical side of the button carries numbers which shows the size of the set dose in a window when the button is screwed outward. When the button is screwed back the unidirectional coupling will transmit the rotation to the driver which has a nut co-operating with a threaded piston rod which is made inrotatable in a housing . This thread connection has a pitch which makes the nut self locking on the piston rod. A set dose may be cancelled by drawing the engaging parts of the ratchet out of engagement against the force of a spring so that the rotation of the button is not transmitted to the driver and then press the button back to the housing . This pen fulfils all the objects mentioned only the dose cancelling procedure is a little troublesome as the dose set button cannot as it will come most naturally just be screwed back if a too large dose is set. Concomitantly forcing the coupling parts apart against the force of the spring and pressing or screwing the button back may be a little difficult and the demand for a spring necessitates use of metal parts in the syringe.

It is an object of the invention to provide a syringe which has the mentioned advantageous features without having the drawbacks known from existing syringes.

This is obtained by an-injection syringes for apportioning set doses of a medicine from a cartridge containing an amount of medicine sufficient for the preparation of a number of therapeutic doses, comprising

- a housing
- a piston rod having a not circular cross-section and an outer thread
- a piston rod drive comprising two elements
  - a) a piston rod guide in relation to which the piston rod is axially displaceable but not rotatable, and
  - b) a nut member which is rotatable but not axially displaceable in the housing and which has an inner thread mating the thread of the piston rod to form a self locking thread connection, a dose setting mechanism comprising a not self locking thread connection along which an injection button by rotation of a dose setting element relative to said housing is screwed out from the proximal end of the housing to project from this proximal end a distance determined by the angle of said rotation and which thread connection by axial returning of the injection button transforms this axial movement to a rotation of one of the piston drive elements relative to the other, which syringe according to the invention is characterised in that a unidirectional coupling is provided between the nut member and the piston rod guide allowing rotation of these parts relative to each other in one direction but not in the opposite direction, the allowed rotation being one by which the piston rod is transported in a distal di rection in the syringe, the coupling being so designed that a set initial reluctance has to be overcome before the rotation takes place.

During the setting of a dose a torque is exerted on the unidirectional coupling in the direction in which this coupling allows rotation after a set initial reluctance has been overcome. As this torque is a weak one resulting when the male and the female part of a not self locking thread connection is rotated relative to each other the initial reluctance can be made large enough to allow this rotation without causing any relative rotation of the parts in the coupling.

When the injection button is pressed the movement of this button is transformed into a rotation of the piston rod (or the nut member) relative to the nut member (or the piston rod). When the button is pressed hard enough the initial reluctans is overcome so that the two elements, the piston rod and the nut member, are rotated relative to each other.

According to the invention a click coupling providing an moderate resistance against rotation is established between the housing and the element rotated relative to the housing to set a dose. Hereby it is ensured that the position corresponding to a set dose is maintained and is not inadvertently altered. The clicks may be taken as an audible signal indicating the size of the set dose.

The unidirectional coupling may be a coupling comprising a pawl sliding over a pawl wheel with teeth having a steep front edge and a ramp shaped trailing edge, and the initial reluctance may be obtained by the fact that the trailing edges of the pawl wheel teeth has a depression engaged by a mating protrusion on the pawl.

A dose scale drum which has in its surface a helical track engaged by a helical rib on the inner side of the housing to form a not self locking thread connection between the housing and the drum may be coupled to the injection button to be moved axially with this button. This way the dose scale drum will be rotated relative to the housing when it is axially displaced with the injection button in said housing.

The thread connection by which the injection button is screwed out from the housing by setting a dose may be the thread connection between the dose scale drum and the housing. In this case the dose scale drum must be coupled to a driver rotating the piston rod (or the nut member) relative to the nut member (or the piston rod) when the injection button is pressed.

A dose is set by rotating an element relative to the housing, and this element may be an element carrying the nut member and the unidirectional coupling so that the rotation is transmitted through said unidirectional coupling to the dose setting drum. The rotation transmitted is in the direction in which the coupling can run free when an initial reluctance is overcome. However, the force needed to screw the dose scale drum up along its thread is not large enough to overcome said reluctance and consequently the rotation is transmitted through the coupling.

In one embodiment of the syringe according to the invention the element rotated relative to the housing may be a part carrying the nut member and the unidirectional coupling through which the rotation is transmitted to the dose setting drum.

In another embodiment of the syringe according to the invention the element rotated relative to the housing may be the injection button and the not self locking thread connection which determines the lifting of the injection button may be an inner thread in a bore in the injection butt on engaging an outer thread on an enlargement of the piston rod. When the injection button is screwed up along the piston rod to project from the housing a torque is exerted on the piston rod trying to rotate this piston rod in a direction which will move it in a distal direction in the syringe. Such a rotation is just the rotation which is allowed by the uniderectional coupling which blocks rotation in the opposite direction. Due to the initial reluctance against rotation of the coupling parts relative to each other the piston rod will not be rotated when the injection button is screwed up along it in a proximal direction in the syringe. If the injection button is screwed in the opposite direction the unidirectional coupling will definitively block a relative rotation of the piston rod and the nut member in the direction which would draw the piston rod in a proximal direction.

In the last mentioned embodiment of the injection syringe the dose scale drum may be mounted rotateable but not axially displaceable on the injection button. When the dose scale drum is moved with the injection button in the axial direction of the syringe the drum will be rotated due to the not self locking thread connection between said drum and the housing so that a number on the drum corresponding to the set dose is visible in a window provided in the wall of the housing. In this embodiment the pitch of the dose drum thread need not be identical with the pitch of the thread along which the injection button is screwed to set a dose, only both thread connections must have a pitch large enough to make the thread connection the not self locking type, i.e. of the type by which an axial movement can be transformed into a rotation.

In an appropriate embodiment of the syringe according to the invention the dose scale drum is mounted rotatable but not axially displaceable on the injection button.

During the injection the injection button must be kept inrotatable but axially displaceable relative to the housing in the angular position to which the injection button is rotated during the setting of a dose. This may be obtained by letting the click coupling between the housing and the injection button comprise protrusions on one part engaging axial grooves in the other. When the injection button is pressed home into the housing the internal thread in the bore of this button will act on the engaging outer thread on the enlargement at the end of the piston rod and convert the axial movement of the injection button to a rotational movement of the piston rod in a direction by which the piston rod is screwed through the nut member in a distal direction in the syringe. The piston rod guide which is connected to one part of the unidirectional coupling is allowed to rotate when the initial reluctance against rotation in the direction else allowed by the coupling is overcome. Also a rotational movement of the dose scale drum is induced by the axial movement of the injection button so that the scale is returned to its zero position when the button is pressed home. When rotation of the dose scale drum and the piston rod is induced by the axial movement of the injection button this button is reacted upon by a torque which must be taken up by the click connection between the injection button and the housing which connection must consequently be strong enough to absorb this force without rotating.

Figure 2:
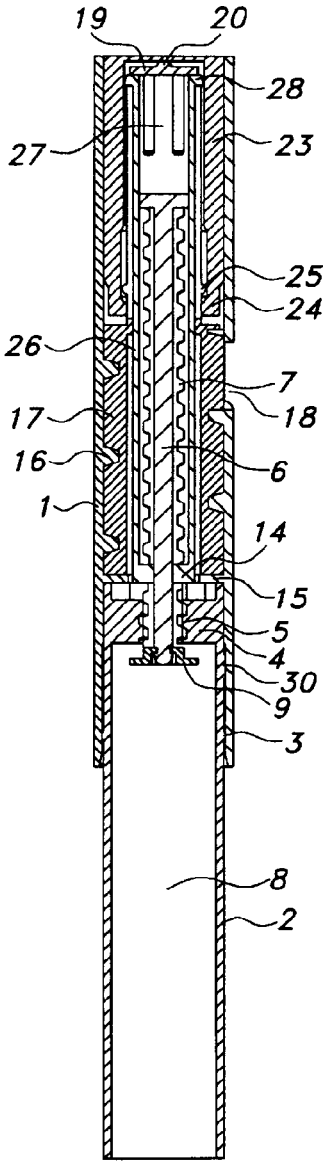
Figure 3:
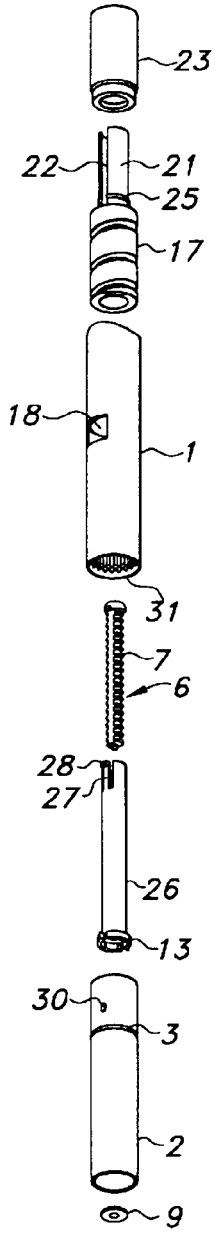
Figure 4:
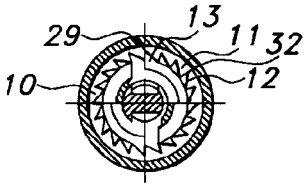
Figure 5:
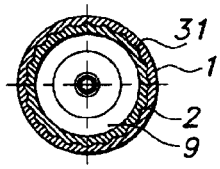
Figure 6:
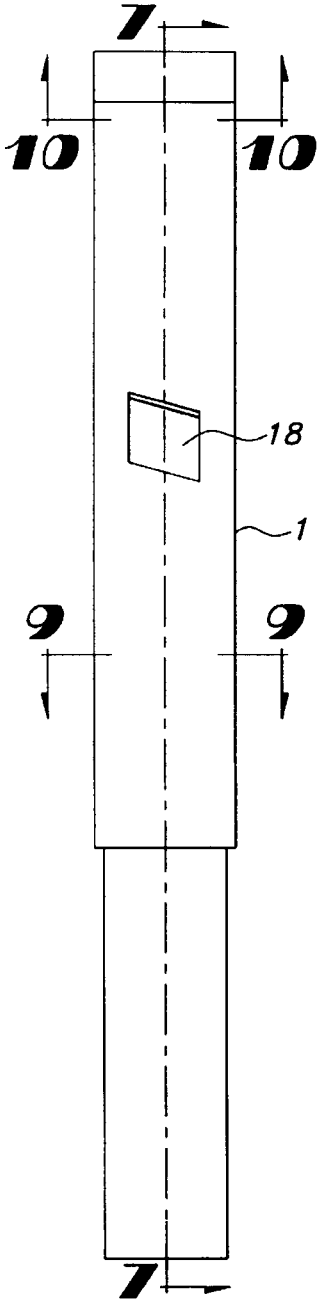
Figure 7:
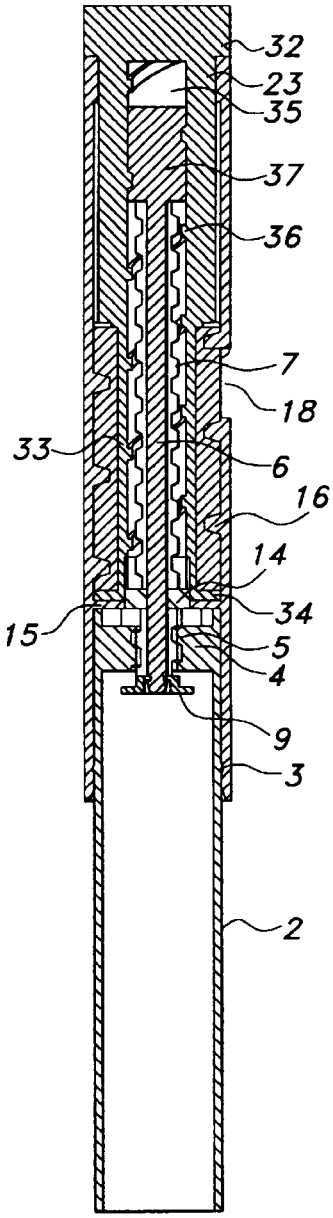
Figure 8:
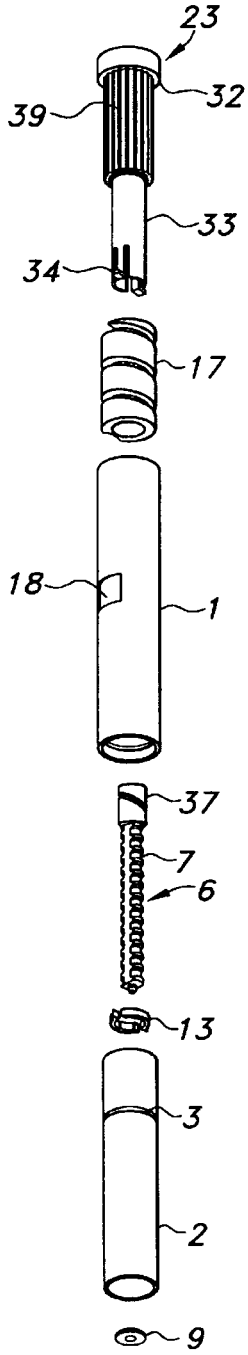
Figure 9:
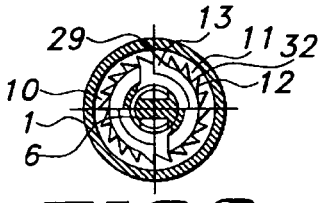
Figure 10:
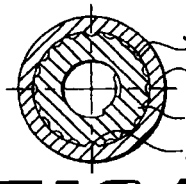

In the following the invention is described in further details with references to the drawing, wherein FIG. 1 shows a front view of an embodiment of an injection syringe according to the invention, FIG. 2 shows a sectional view along the line II-II in FIG. 1, FIG. 3 shows in a reduced scale an exploded view of the syringe in FIG. 1, FIG. 4 shows a sectional view along the line IV-IV in FIG. 1, FIG. 5 shows a sectional view along the line V-V in FIG. 1, FIG. 6 shows a front view of another embodiment of an syringe according to the invention, FIG. 7 shows a sectional view along the line VII-VII in FIG. 6, FIG. 8 shows in a reduced scale an exploded view of the syringe in FIG. 6, FIG. 9 shows a sectional view along the line IX-IX in FIG. 6, FIG. 10 shows a sectional view along the line X-X in FIG. 6.

Figure 11:
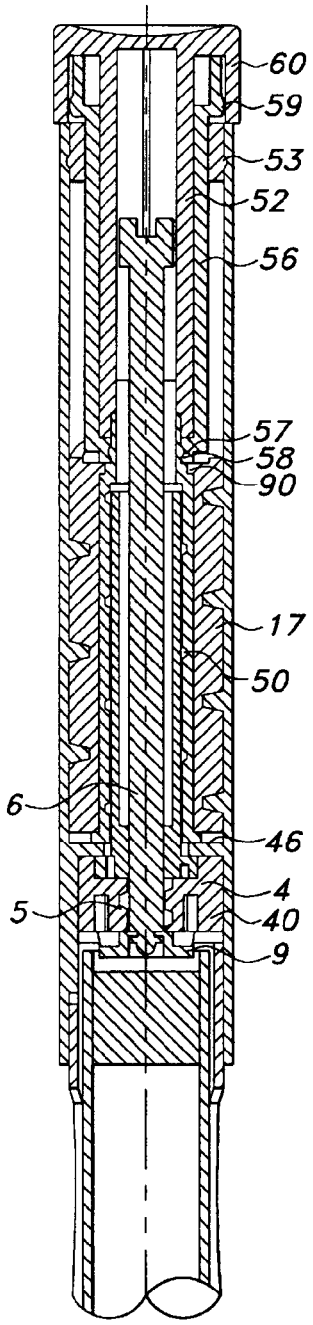
Figure 12:
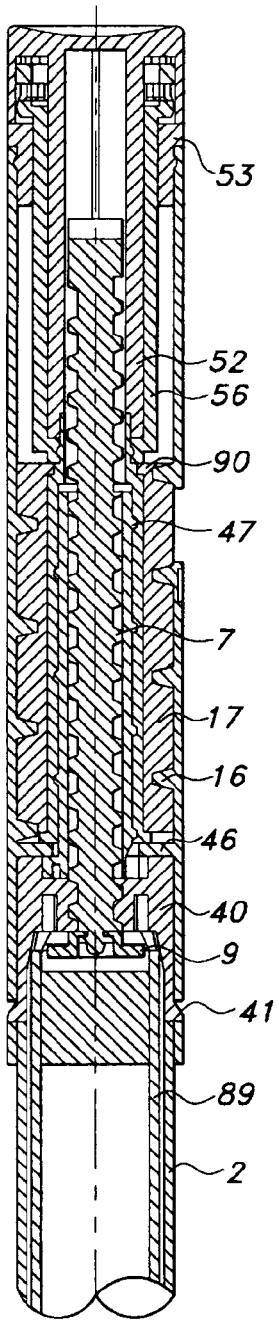
Figure 13:
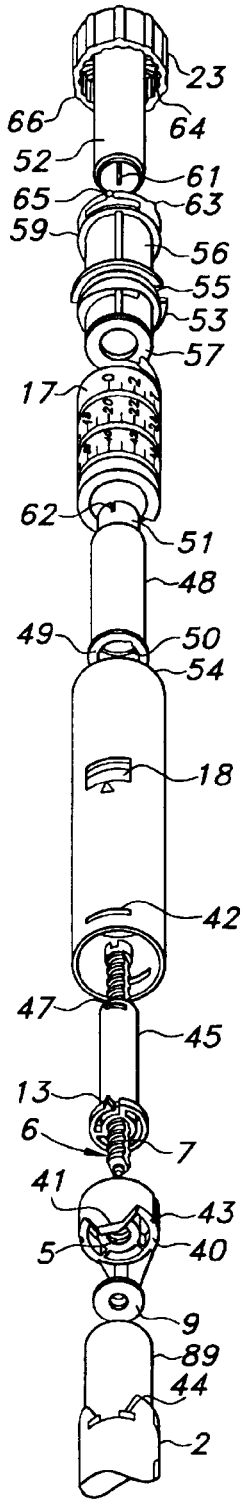
Figure 14:
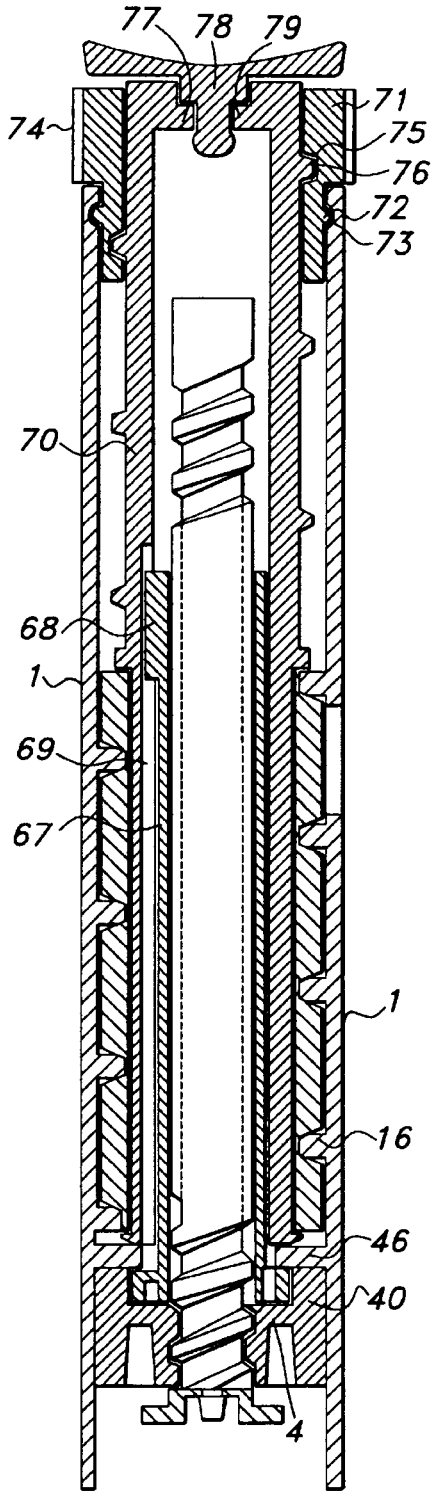
Figure 15:
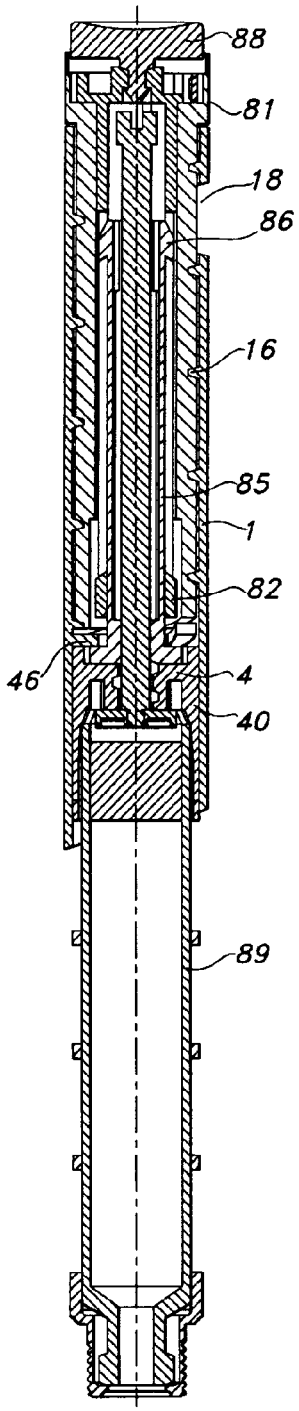
Figure 16:
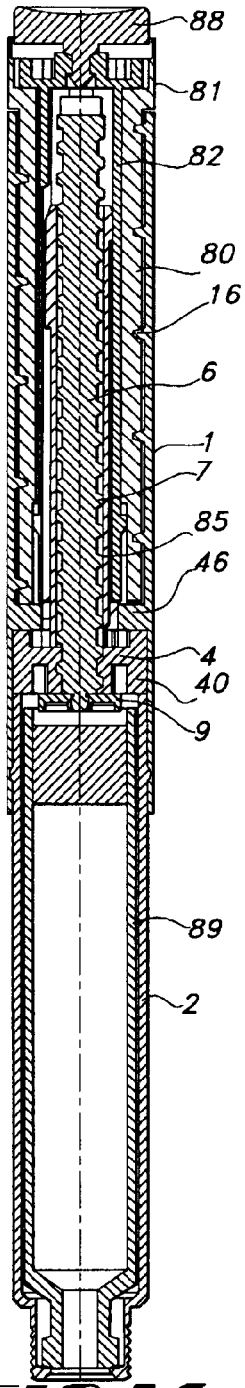
Figure 17:
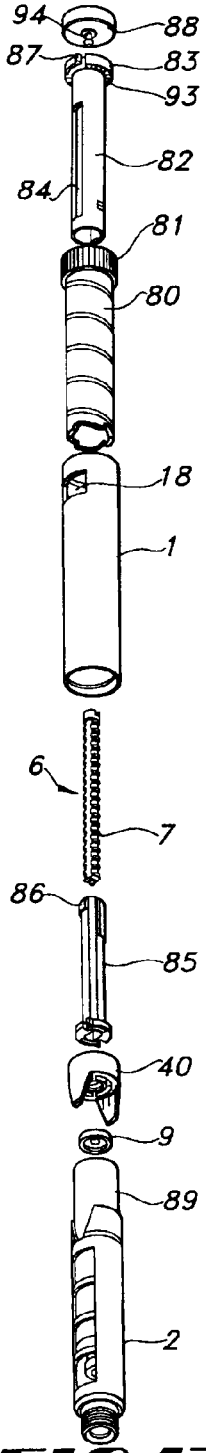

FIG. 11 shows a sectional side view of another embodiment of a syringe according to the invention, FIG. 12 shows a sectional side view perpendicular to the view in FIG. 11, FIG. 13 shows in a reduced scale an exploded view of the syringe in FIGS. 11 and 12, FIG. 14 shows a sectional side view of the dose setting part of another embodiment of a syringe according to the invention, FIG. 15 shows a sectional side view of still another embodiment of a syringe according to the invention, FIG. 16 shows a sectional side view perpendicular to the view in FIG. 15, FIG. 17 shows in a reduced scale an exploded view of the syringe in FIGS. 15 and 16, Initially it may be convenient to define that in this application directions of rotation are always seen from the proximal end of the pen and designed as clockwise or anticlockwise seen in this direction.

FIG. 1 shows an injection syringe of the kind by which a liquid from an ampoule can be apportioned in a number of individually set does. FIG. 3 shows an exploded view of this syringe and the FIGS. 2, 4 and 5 sectional views taken along different lines in FIG. 1.

The syringe comprise a tubular housing 1 which is by a partition 15 divided into a first and a second division into the first one of which an ampoule holder 2 is snapped by a snap lock comprising a ring shaped bead 3 on the ampoule holder 2 which bead is snapped into a corresponding circumferential grove in the inner wall of the housing 1 near an open end thereof. By this snap connection the ampoule holder 2 is secured in the housing 1 so that it can be rotated but not axially displaced relative to this housing.

In the syringe ready for use an ampoule is mounted in the ampoule holder which is then at its distal end closed by an end wall provided with a needle hub receiving part onto which a needle hub can be mounted having a needle with one end communicating with the content of the ampoule and the other end free to be inserted into a patient. In the shown syringe, however, neither ampoule, end wall nor needle hub are shown.

The end of the ampoule holder 2 inserted in the housing 1 is closed by a wall 4 having a central bore with an internal thread 5. A piston rod 6 having an external thread 7 mating the thread 5 of said bore extends through said bore. The threads are so designed that a clockwise rotation of the piston rod will drive this rod into an ampoule accommodating compartment 8 in the first division of the housing 1. At its end projecting into the compartment 8 the piston rod 6 is provided with a pressure foot 9 designed to abut a piston closing the rear end of an ampoule accommodated in the ampoule holder 2.

In the proximal side of the end wall 4 the bore is enlarged and the internal side of the enlargement is provided with pawl wheel teeth 10 having a steep front edge 11 facing the clockwise direction and a ramp shaped rear edge 12 facing the anticlockwise direction. At least one pawl 13 mounted on a piston rod guide 14 co-operates with the pawl teeth 10 so that said piston rod guide can only be rotated clockwise in the ampoule holder 2.

On the inner wall of the second division of the housing 1 a helical protruding rib 16 is provided defining an inner thread with a high pitch. A dose scale drum 17 is in its outer wall provided with a helical grove defining a corresponding external thread mating the inner thread just mentioned. The pitch angle of the threads exceeds the angle of friction for the materials forming the parts of the thread connection and consequently the thread connection is of the not self locking type which induce a relative rotation of the parts of the connection when these part are moved axially relative to each other.

Numbers indicating set doses are printed on the outer wall of the dose drum 17 and the number corresponding to a set dose is shown in a window 18 provided in the side wall of the housing 1.

The dose scale drum 17 is provide with a tubular extension 21 having an end near the proximal end of the syringe. Said end of the extension is closed by an end wall 19 having a central outer protrusion 20. In a part of the wall adjacent to the end wall 19 the extension 21 is provided with slots 22. The said end of the extension is covered by a cup shaped cap 23 forming an injection button. Internal hooks 24 at the open end of this cap snaps over an external circumferential bead 25 on the extension 21 and the protrusion 20 on the end wall 19 abuts the inner side of the bottom of the cap 23 to form a journal about which the injection button can rotate relative to the extension 21 whereas it cannot be axially displaced relative to this extension.

A driver tube 26 integral with the piston rod guide 14 extends from this piston rod guide to the end wall 19 of the dose scale drum extension 21 and is at its proximal end divided into tongues 27 terminated by external hooks 28 engaging the slots 22 ill the extension 21. This way the dose scale drum 17 is bound to rotate with the driver tube 26 but is axially displaceable relative to this tube.

To set a dose the ampoule holder 2 is rotated anticlockwise in the first division of the housing 1. This rotation is performed against a resistance presented due to the fact that a protrusion 30 on the outer wall of the ampoule holder rests in one of a number of depressions 31 circumferentially provided in the inner wall of said first division of the housing as shown in the cross-sectional view in FIG. 3. The angular spacing of the depressions are appropriately made so that a dose of one unit is set when the protrusion is moved from one depression to the neighbouring depression so that the number of clicks heard and felt during the dose setting rotation corresponds to the size of the set dose.

The rotation of the ampoule holder is due to the friction in the engaging threads 5 and 7 transmitted to the piston rod 6 and further through the unidirectional coupling to the piston rod guide 14 although the torque is transmitted in a such a direction that the pawl will intend to click over the pawl wheel teeth 10. However, before this click function is performed a reluctance have to be overcome. This reluctance is obtained by providing the pawl 13 with a protrusion 29 at its end engaging the pawl wheel teeth 10 and by providing depressions 32 in the ramp shaped edges 12 of the pawl wheel teeth into which depressions the protrusion 29 on the pawl 13 will rest. Before the clicking release of the coupling is obtained a torque sufficient to lift up the protrusion 29 of the pawl 13 from the depression 32 in the ramp shaped edge 12 must be provided. Altogether a moderate torque can be transmitted from the rotated ampoule holder 2 to the driver tube 26. As the hooks 28 at the proximal end of the driver tube 26 engage the slots 22 in the dose scale drum extension 21 the dose scale drum will be rotated and be screwed upwards in the second division of the housing 1 and the injection button 23 will be lifted to protrude from the proximal end of the housing 1. As only a small torque is needed to screw up the dose scale drum this is obtained without releasing the unidirectional coupling to its clicking release function mode. The size of the set dose can currently be seen on the part of the dose scale drum which is presented in the window 18. If a too large dose has been set the ampoule holder can be rotated in a clockwise direction until the number corresponding to the size of the wanted doe is presented in the window 18.

To inject the set dose the injection button 23 is pressed home into the housing 1. Thereby the dose scale drum 17 is pressed in the distal direction and due to the thread connection between said drum and the housing 1 a torque is exerted on the drum rotating this drum in a clockwise direction. Said torque is via the slots 22 in the drum extension 21 and the hooks 28 at the end of the driver tube 26 and this tube itself transmitted to the piston rod guide 14. The pawls 13 on the piston rod guide are allowed to rotate in the clockwise direction when the torque is strong enough to overcome the reluctance provided by the protrusions 29 on the pawls engaging the depressions 32 in the ramp shaped edges of the pawl wheel teeth.

Such a strong torque is provided if only the inject button 23 is pressed hard enough. The piston rod guide 14 will now rotate clockwise with the unidirectional coupling working in its clicking released mode and the piston rod will be rotated clockwise too and will thereby be screwed through the wall 4 further into the ampoule accommodating compartment 8. The unidirectional coupling will never allow an anticlockwise rotation of the piston rod guide and the piston and this way it is ensured that the pressure foot 9 will never be drawn out of abutment with the piston in a not shown ampoule in the compartment 8.

In the shown embodiment the end wall 4 with its threaded bore forms a nut member relative to which the piston rod is rotated by the piston rod guide 14 and the driver tube 26. Embodiments may be imagined wherein the piston rod guide is provided in the wall 4 and a nut element is rotated by the driver tube and such embodiment will not be beyond the scope of the invention.

Another embodiment is described with reference to the FIGS. 6-10. Elements corresponding to elements in the embodiment described with references to the FIGS. 1-5 are provided with the same reference numbers. Different from the embodiment in FIG. 1-5 is the fact that the injection button 23 and not the dose scale drum 17 is provided with an extension 33, and that the driver tube 26 is omitted. Further the injection button 23 is provided with a flange 32 which abuts the end of the housing when the injection button is pressed home. The extension 33 serves as a journal for the dose scale drum 17 which is free to rotate on this journal but bound to follow axial movements of the injection button 23 due to hooks 34 at the end of the extension 33. A longitudinal bore 35 in the injection button and its extension 33 is provided with an internal helical rib 36 engaging a corresponding helical groove in an enlargement 37 at the proximal end of the piston rod to form a thread connection between said button 23 and said piston rod 6. The pitch of this thread connection is so that a not self locking thread connection is formed.

To set a dose the injection button 23 is manually rotated in a clockwise direction Thereby this button is screwed outwards from the housing 1 as the piston rod 6 will through the piston rod guide 14 and the unidrectional coupling be kept inrotatable although said unidirectional coupling in influenced by a torque in its release direction, however, due to the provided initial reluctance the piston rod guide 14 will not immediately be rotatable. In its movement outwards the injection button 23 will draw the dose scale drum 17 with it. When this drum is moved axially in the housing it will be rotated due to the not self locking thread connection between said drum 17 and the housing 1.

By this construction the thread along which the injection button is screwed outwards and the tread along which the dose scale drum is rotated in the housing may be different.

A click connection corresponding to the one established between the cartridge holder 2 and the housing 1 in the embodiment according to FIG. 1 is in the embodiment according to FIG. 6 appropriately provided between the injection button 23 and the housing 1 where one or more protrusions 38 provided on the inner wall of the housing engages grooves 39 in a cylindrical outer wall of the button 23. Thereby axial movement of the injection button is allowed in all its possible angular positions.

When the injection button is pressed to inject a set dose said button will be maintained inrotatabie during its axial movement as the locking between the above mentioned protrusions on the inner wall of the housing and grooves on the outer wall of the button is strong enough to absorb the torque exerted on the injection button when it drives the piston rod to rotation in a clockwise direction after having overcome the reluctance against rotation in the release direction of the unidirectional coupling.

The embodiment shown in FIGS. 11, 12 and 13 has the housing 1 with the window 18. The end wall 4 with the internal thread 5 is provided in a separate member 40 which is mounted in an end of the housing, the member 40 having protrusions 41 engaging slots 42 in the housing to lock the member 40 to the housing 1. Further the member 40 has at its periphery longitudinal recesses 43 which are engaged by not shown internal ribs in the housing to lock the member 40 against rotation relative to the housing 1. Further protrusions 44 on the ampoule holder 2 engage the slots 42 to lock the ampoule holder 2 to the housing 1.

The piston rod 6 engages by its external thread 7 the internal thread of the end wall 4 and is at its end in the ampoule holder terminated by a pressure foot 9 relative to which the piston rod 6 is rotatable. A driver tube 45 is at one end provided with the pawl 13 which engages pawl wheel teeth in the member 40 and is held between a ring shaped wall 46 in the housing and the end wall 4 in the member 40 to keep the driver tube 45 from axial movement but allowing it to rotate. On its inner wall the driver tube 45 has a key engaging a longitudinal recess in the piston rod 6. Thereby rotation of the driver tube is transmitted to the piston rod 6 whereas the piston rod can move freely in the axial direction of the driver tube 45. On its outer wall the driver tube 45 has an outer thread 47 which engages an inner thread 50 in a nut member 48 which has at its distal end a flange 49 and is at its proximal end provided with a part 51 with reduced diameter to which part one end of a tubular part 52 which at its other end carries a button 23 is secured.

In the proximal end of the housing 1 a bushing 53 is secured to be non rotatable an non displaceable relative to said housing 1 the rotational locking being obtained by lugs 54 at the proximal end of the housing engaging recesses 55 at the periphery of the bushing 53. A guide member 56 is longitudinally displaceable in the bushing 53 but inrotatable relative to said bushing and consequently relative to the housing 1. The guide member has at its distal end an annular end wall 57. The part 51 of the nut member 48 is passed through the opening of said end wall 57 and has a bead 58 gripping into a circumferential inner recess in the wall of annular opening through said end wall to keep the bushing 53 secured to said part 51 so that this part can be rotated but not axially displaced in relation to the bushing 53. The scale drum 17 is journalled on the nut member 48 and is held on this nut member by having a flange 90 held between the end wall 57 of the guide member 56 and the shoulder formed where the part 51 connects to the nut member 48.

The button 23 is held rotatably on the guide member 56 which has a ring bead 59 engaging a circumferential recess 60 in the inner wall of the button 23 which recess 60 is somewhat broader than than the bead 59 so that the button in excess of being rotatable on said bushing 53 can be axially displaced a distance defined by the width of the recess 60 relative to the width of the bead 59. The button 23 is coupled to the nut member 48 by internal ribs 61 in the tubular part 52 engaging slots 62 in the proximal part of the part 51 of the nut member 48. This coupling forces the button 23 and the nut member 48 to follow each other in rotational movements but allow a minor relative axial displacement.

The proximal end surface of the guide member 56 has one or more axially directed protrusions 63 which can co-operate with radial recesses 64 in the bottom of the button 23, but mainly a biasing keeps these recesses and protrusions out of engagement. Further the guide member has at its proximal end at least one radial protrusion 65 which is biased to engage axial recesses 66 in an inner wall of the button to produced a click sound each time the button is rotated relative to the bushing so that the protrusion jump from one recess to the neighbour recess.

To set a dose the button 23 is rotated in a clockwise direction. This rotation is due to the coupling between the ribs 61 and the slots 62 transmitted to the nut member 48 which is then screwed in distal direction along the driver tube 45 which is held inrotatably in the housing due to the reluctans of the pawl 13 to move along the pawl teeth in the member 40. The movement of the nut member 48 in proximal direction makes the scale drum 17, the guide member 56, and the tubular part 52 with the button move in proximal direction so that the button is elevated over the end proximal end of the housing 1. A to high set dose can be reduced by rotating the button in an anti clockwise direction.

During the rotation of the button the radial protrusion 65 of the guide member 56 clicks from one axial recess 66 to the other. The distance between can appropriately be chosen so that a click corresponds to a changing of the set dose by one international unit up or down. Due to engagement between the helical grove on the cylinder wall of the scale drum and a helical rib on the inner wall of the housing the movement of the dose scale drum 17 will rotate and displace said drum so that the set dose is shown in the window 18.

When the dose scale drum is displaced outwardly in the housing a steep front side of a saw tooth 91 at the proximal end of the dose scale drum 18 will abut a steep front side of a similar tooth 92 on the bushing whereby the rotation of the dose scale drum is stopped to indicate that a maximum dose has been set.

To inject the set dose the button 23 is pressed. Thereby the bias keeping the protrusions 63 and the recesses 64 out of engagement is overcome and the said engagement is established. The button 23 is now locked relative to the guide element 56 which is again locked against rotation relative to the bushing 53 and consequently relative to the housing 1. The coupling between the tubular part 52 and the nut member 48 makes this nut member inrotatable relative to the housing so an axial movement of said nut member in a distal direction will due to the not self locking thread coupling between this nut element and the driver tube 45 make this driver tube 45 rotate in a clockwise direction and due to the key/groove coupling between the driver tube 45 and the piston rod 6 said piston rod will be screwed through the end wall 4 further into the ampoule holder compartment. The locking of the button 23 against rotation during the injection ensures that the set dose is not inadvertently changed during the injection.

In the embodiment shown in FIG. 14 separate buttons are provided for the dose setting and the injection. Corresponding to previously described embodiments this one has a housing 1 and a driver tube 67 which is rotatable in only one direction due to a pawl which engage pawl wheel teeth in a part secured in the distal end of the housing. Trapping of the pawl between the member 40 and a ring shaped wall 46 in the housing fixes the driver tube against axial movement. On the outer wall of the driver tube 67 an axial rib 68 is provided which rib engages an axial recess 69 in a tubular injection element 70 to transmit rotation of said injection element to the driver tube 67.

At the proximal end of the housing 1 a dose setting button 71 is mounted so that this button can be rotated but not axially displaced relative to the housing 1. This is obtained by the fact that the dose setting button 71 on a part fitting into the housing has a ring shaped bead 72 which engages a mating circumferential recess 73 in the inner wall of the housing. Outside the housing the dose setting button has a part having a diameter corresponding to or being larger than the diameter of said housing which part can be provided with axial ribs 74 to ensure a good grip by the setting of a dose. The dose setting button 71 has a central bore the inner wall of which has a helical recess 75 engaging a helical rib 76 provided on the outer wall of the proximal part of the injection element 70 which element passes through the bore of the dose setting button 71. The outer wall of the distal part of the injection element 70 forms a journal for the scale drum 17 which through an outer helical recess engaged by an internal helical rib 16 in the housing is rotated to show the set dose in the window 18 when the scale drum is displaced axially in the housing. The proximal end of the injection member is terminated by an end wall 77 which carries an injection button 78 which is by a pivot pin 79 journaled in a central bore in said end wall 77.

To set a dose the dose setting button 71 is rotated in a clockwise direction. As the injection member is kept non rotatable by its coupling to the driver tube 67 the collaboration between the helical recess 75 in the inner wall of the dose setting button 71 and the helical rib 76 on the outer wall of the injection element 70 will screw the injection element out through the dose setting button so that the injection button 78 is lifted up from the proximal end of the housing. Although the driver tube 67 with its pawl can be rotated in the clockwise direction an initial torque is needed which is larger than the torque transmitted from the dose setting button to the injection element.

To inject a set dose the injection button 78 is pressed and the injection element is moved back into the housing. The co-operation of the helical recess 75 in the inner wall of the dose setting button 71 and the helical rib 76 on the outer wall of the injection element 70 will now make the injection element rotate in a clockwise direction and if only the injection button is pressed hard enough a torque is produced large enough to overcome the initial reluctance of the pawl mechanism against rotation in said clockwise direction.

The separation of the dose setting button 71 and the injection button 78 makes it less likely that the dose setting button is inadvertently operated during the injection.

FIGS. 16 and 17 illustrates still another embodiment. To maintain a clockwise rotation of a dose setting button for increasing the set dose the pawl mechanism working between the driver tube and the housing is turned so that it bars clockwise rotation and reluctantly allows anticlockwise rotation of the driver tube. Further the thread of the piston rod and the thread in the end wall of the housing is so designed that an anticlockwise rotation of the piston will screw the piston rod through said end wall and into the cartridge holder compartment. The piston rod has a not round cross-section and fits through the driver tube bore which has a corresponding not round cross-section. This way rotation is transmitted whereas the piston rod is allowed to move longitudinally through the driver tube.

A scale drum 80 is in its outer wall provided with a helical track which is engaged by a helical rib 16 along the inner wall of the housing 1. At its proximal end the scale drum 80 has a diameter exceeding the inner diameter of the housing to form a dose setting button 81 which on its cylindrical outer wall is knurled to ensure a good finger grip.

A bushing 82 having a flange 83 at its proximal end and having a pair of opposite longitudinal slots 84 through its side walls fits into the scale drum 80 and over the driver tube 85 which tube has on its outer wall hooks 86 engaging the slots 84 of the bushing 82 whereby the bushing 82 and the driver tube 85 is coupled to each other so that rotation but not longitudinal displacement is transmitted between said two elements.

In the dose setting button a compartment is provided having a cylindrical side wall circumferentially provided with longitudinal recesses and a bottom with a rosette of teeth having a triangular cross-section. The flange 83 of the bushing 82 is adopted in said compartment and has at its periphery a radial protrusion 87 which is biased toward the side wall of the compartment. At its distal side the flange 83 has a rosette 93 of teeth which can be brought into engagement with the rosette at the bottom of the compartment.

The bushing 82 is mounted in the scale drum 80 with protrusion on the outer wall of the bushing 82 engaging recesses in the inner wall of the scale drum 80 so that a limited movement of the bushing in the scale drum is allowed so that the bushing can be moved axially relative to the scale drum to make or not make the teeth of said rosettes engage each other. An injection button 88 is rotatably mounted with a pivot pin 94 journaled in an end wall of the bushing 82.

When a dose is set by rotating the dose setting button 81 in a clockwise direction, the scale drum is screwed out of the housing and the dose setting button is lifted away from the proximal end of the housing. The bushing is kept non rotated due to its coupling to the driver tube which is locked against clockwise rotation and if a set dose is reduced by rotating the dose setting button 81 in an anticlockwise direction the pawl mechanism working between the driver tube and the housing is sufficient reluctant to rotate in its not blocking direction to prevent the bushing 82 from following this anticlockwise rotation. Therefore by the rotation of the dose setting button 81 in any direction the radial protrusion 87 on the flange 83 of the bushing 82 will click from one of the axial recess in the inner wall of the dose setting button 81 to the next one, the recesses being so spaced that one click corresponds to a chosen change of the set dose, e. g. one unit or a half unit. During the setting the rosette in the dose setting button forces the rosette 93 on the flange 83 of the bushing 82 out of engagement.

When the injection button 88 is pressed to inject the set dose the said rosettes are pressed into engagement so that the bushing 82 will follow the anticlockwise rotation of the dose setting button 81 which is induced by the thread engagement between the helical track of the scale drum 80 and the rib 16 in the housing when the scale drum 80 is pressed back into said housing. The bushing will rotate the driver tube 85 in an anticlockwise direction which the pawl mechanism reluctantly allows an the piston rod is thereby screwed further into an ampoule 89 in the ampoule holder 2.

By this device the risk for inadvertent operation of the dose setting button 81 during the injection is eliminated. Further the device consist of a minimum of parts whereby the manufacturing is made easy.

What is claimed is:

1. A medication delivery pen comprising:

a housing having proximal and distal ends and including a holder for containing a cartridge containing a medication to be delivered through a conduit connected to the cartridge[.];

a piston rod having a not circular cross-section and an outer thread[, and];

a piston rod drive for driving said piston rod in a distal direction inside the cartridge, said piston rod drive including a first part rotatably mounted within said housing and mating with the not circular cross-section of said piston rod, and a second part integral with said housing and having an internal thread mating the thread of said piston rod to form a [self-locking] thread connection, wherein rotation of said first part in a first direction relative to said second part drives said piston rod in a distal direction; and a one-way coupling comprising:

a) an annular ring of equally spaced internal ratchet notches situated on the inside of said housing, which internal notches have a steep front edge and a ramp shaped trailing edge, b) a pawl surrounding said piston rod and having at least a pair of resilient arms, each arm having a free end, said pawl being connected with said first part of said piston rod drive, and c) means situated on said free end of each arm for engaging in the internal ratchet notches of said annular ring, which means abuts said steep front edge of said internal notches, thereby preventing said pawl body from rotating in one direction relatively to said housing, the prevented direction being one by which the piston rod would be transported in a proximal direction;

*wherein in situation of use, the piston rod does not rotate and advance axially when a dose setting member is rotated in either a clockwise or anticlockwise direction unless an axial force is applied to the pen, wherein when the axial force is applied to press an injection button home, the axial force is transformed to result in rotation*

*of the piston rod in a direction which in turn causes the piston rod to advance distally.*

2. A medication delivery pen according to claim 1, wherein said two or more arms are disposed with the same relative spacing around the circumference of said pawl.

3. A medication delivery pen according to claim 1, wherein said steep front edges of said internal notches on opposite sides of said annular ring are parallel to each other.

4. A medication delivery pen according to claim 1, wherein said arms extend circumferentially from a body portion of said pawl and wherein said means situated on said free end of each arm is the end-surface of the arm lying circumferentially opposite said pawl and abutting said steep front edge of said internal notches.

5. A medication delivery pen according to claim 1, wherein said arms extend circumferentially from said pawl body and wherein said means situated on said free end of each arm includes a protrusion.

6. A medication delivery pen comprising:

a housing having proximal and distal ends and including a holder for containing a cartridge containing a medication to be delivered through a conduit connected to said cartridge[,]*;* a piston rod having a not circular cross-section and an outer thread[, and]*;* a piston rod drive for driving said piston rod in a distal direction inside the cartridge, said piston rod drive including [a first part having an internal thread mating the thread of said piston rod to form a self-locking thread connection, and a second part integral with said housing and mating with the not circular cross-section of said piston rod,] *a first part rotatably mounted within said housing and mating with the not circular cross-section of said piston rod so that the piston rod rotates with the first part but the piston rod may move axially independent of the first part, and a second part integral with said housing and having an internal thread mating the thread of said piston rod to form a thread connection* wherein rotation of said first part in a first direction relative to said second part drives the piston rod in a distal direction; [and]

a one-way coupling comprising:

a) an annular ring of equally spaced internal ratchet notches situated on the inside of said housing, which internal notches have a steep front edge and a ramp shaped trailing edge, b) a pawl surrounding said piston rod and having at least a pair of resilient arms, each arm having a free end, said pawl being connected with said first part of said piston rod drive, and c) means situated on said free end of each arm for engaging in the internal ratchet notches of said annular ring, which means [abuts] *engages in said internal notches by* (*i*) *abutting* said steep front edge of the internal notches, thereby preventing said pawl body *and said first part of said piston rod drive* from rotating in [one direction relatively to said housing] *a direction opposite to said first direction*, the prevented direction being one by which the piston rod would be transported in a proximal direction*, and* (*ii*) *resting along the ramp shaped trailing edge of the internal notches, thereby providing an initial reluctance that has to be overcome by a sufficiently strong rotational torque before said pawl body and said first part of said piston rod drive can rotate in the first direction; and*

*a dose setting mechanism comprising a not self locking thread connection along which an injection button by rotation of a dose setting element relative to the housing is screwed out from the proximal end of the housing and which thread connection by axially returning the injection button in a distal direction back into the housing transforms said axial movement to a rotational torque on the first part of the piston rod drive and said pawl causing said first part to rotate in a the first direction, provided that the rotational torque is strong enough to overcome the initial reluctance provided by the one-way coupling;*

*wherein a set dose may be reduced in size without having to axially pull apart any parts of the pen.*

7. A medication delivery pen according to claim 6, wherein said two or more arms are disposed with the same relative spacing around the circumference of said pawl.

8. A medication delivery pen according to claim 6, wherein said steep front edges of said internal notches on opposite sides of said annular ring are parallel to each other.

9. A medication delivery pen according to claim 6, wherein said arms extend circumferentially from a body portion of said pawl and wherein said means situated on said free end of each arm is the end-surface of the arm lying circumferentially opposite said pawl and abutting said steep front edges of said internal notches.

10. A medication delivery pen according to claim 6, wherein said arms extends circumferentially from said pawl body and wherein said means situated on said free end of each arm includes a protrusion.

11. A medication delivery pen comprising:

a housing having proximal and distal ends and including a holder for containing a cartridge containing a medication to be delivered through a conduit connected to said cartridge[.]*;* a piston rod *that is rotatable during injection of the medication, said piston rod* having a not circular cross-section and an outer thread[, and]*;* a piston rod drive for *rotating the piston rod during injection, thereby* driving said piston rod in a distal direction inside the cartridge, said piston rod drive including a first part having an internal thread mating the thread of said piston rod to form a [self-locking] thread connection, a second part mating with the not circular cross-section of said piston rod, wherein said first and second parts are rotatable relative to one another to drive the piston rod in an axial direction; and a one-way coupling comprising:

a) an annular ring member of equally spaced internal ratchet notches, and b) a pawl member having at least a pair of resilient arms, each arm having a free end for engaging said ratchet notches so as to allow rotation between said ring and said pawl in a first rotational direction and prevent rotation between said ring and said pawl in a second rotational direction, wherein said members are coupled between said housing and said piston rod drive such that rotation between said members in said first rotational direction causes the piston rod to move in a distal direction, and such that said members prevent movement of said piston rod in said proximal direction*;*

*wherein in situation of use, the piston rod does not rotate and advance axially when a dose setting member is rotated in either a clockwise or anticlockwise direction unless an axial force is applied to the pen, wherein when the axial force is applied to press an injection button home, the axial force is transformed to result in rotation*

*of the piston rod in a direction which in turn causes the piston rod to advance distally.*

*12. An injection device comprising:*

*a housing for holding a cartridge of medication, the housing having a distal end and a proximal end;*

*a threaded piston rod that is rotatable during injection of the medication, said piston rod having a not-circular cross-section;*

*a piston rod drive for rotating said piston rod during injection, thereby driving said piston rod in a distal direction inside the cartridge, said piston rod drive comprising:*

*a first rotatable part that engages the not-circular cross-section of the piston rod so as to allow rotation of the piston rod to accompany rotation of the first part while allowing the piston rod to move proximally and distally with respect to the first part;*

*a second part that engages the threads on the piston rod and is fixed in the housing, thereby causing the piston rod to move distally when the piston rod is rotated in a first direction; and*

*a one way coupling for allowing the first part to rotate in the first direction and thereby drive the piston rod to move distally but prevents the piston rod from rotating in a second direction that would cause the piston rod to move proximally;*

*wherein in situation of use, the piston rod does not rotate and advance axially when a dose setting member is rotated in either a clockwise or anticlockwise direction unless an axial force is applied to the device, wherein when the axial force is applied to press an injection button home, the axial force is transformed to result in rotation of the piston rod in a direction which in turn causes the piston rod to advance distally.*

*13. A dose injecting apparatus for an injection device that comprises a cartridge of medication from which multiple doses of medication are apportioned and a dose scale drum means for indicating the size of a set dose and for indicating that the apportioned set dose has been delivered; the dose injecting apparatus comprising:*

*a rotatable piston rod that rotates only during injection of medication, wherein the rotatable piston rod comprises a distal portion having an external thread disposed thereon and wherein the piston rod has a proximal portion opposite the distal portion;*

*a first part comprised of a rotatable tubular member that engages and causes the rotatable piston rod to rotate during injection of medication;*

*a second non-rotatable part fixed to a housing, the second part having an internal thread engaging the thread on the distal portion of the rotatable piston rod so that when the rotatable piston rod rotates it screws through the internal thread of the non-rotating second part; and*

*wherein during injection of medication:*

*(i) the piston rod rotates only in one direction, that direction being one that induces the piston rod to move axially in a distal, medication expelling direction and not in a direction that would induce the piston rod to move in a proximal direction, and*

*(ii) the piston rod advances distally to expel medication as a result of the screwed engagement of the thread on the distal portion of the piston rod with the internal thread of the non-rotatable part;*

*wherein in situation of use, the piston rod does not rotate and advance axially when a dose setting member is rotated in either a clockwise or anticlockwise direction unless an axial force is applied to the device, wherein when the axial force is applied to press an injection button home, the axial force is transformed to result in rotation of the piston rod in a direction which in turn causes the piston rod to advance distally.*

*14. The dose injecting apparatus of claim 13, wherein the proximal portion of the piston rod contains a helical thread that is different than the thread on the distal portion and wherein the tubular member has in its interior a corresponding helical thread that engages the helical thread on the proximal portion of the piston rod, and wherein the threaded engagement between the tubular member and the thread on the proximal portion of the piston rod cause the rotation of the piston rod during injection of medication.*

*15. The dose injecting apparatus of claim 13, wherein the tubular member has an interior that engages a non-circular portion of the piston rod so that when the tubular member rotates during injection of medication, it rotates the piston rod.*

*16. The dose injecting apparatus of claim 15, wherein the tubular member has a thread on its outer surface.*

*17. An injection mechanism for expelling a dose of medication from a cartridge contained in a syringe that has a housing, the injecting mechanism comprising:*

*a piston rod that is rotatable during injection of the medication, said piston rod for exerting a force on the cartridge during said injection;*

*a piston rod driver for rotating said piston rod during injection, thereby driving the piston rod in a distal direction inside the cartridge; and*

*a dose dial drum for setting a dose of medication, the dose dial drum axially displaceable relative to the syringe housing in a proximal axial direction by rotating it in a first direction and being axially displaceable in a distal axial direction by rotating it in a second direction opposite the first direction, the dose dial drum being coupleable to the piston rod driver; and*

*wherein the dose dial drum and the piston rod driver are releasably coupleable to each other so that when the dose dial drum and the piston rod driver are coupled together during dose injection, they rotate together but when they are decoupled during dose setting the dose dial drum can rotate independently of and relative to the piston rod drive and wherein during injection of the dose, the piston rod is rotated and screwed through the housing via a threaded engagement between the piston rod and a threaded element fixed relative to the housing;*

*wherein in situation of use, the piston rod does not rotate and advance axially when a dose dial drum is rotated in a dose-reducing direction unless an axial force is applied to the mechanism, wherein when the axial force is applied to press an injection button home, the axial force is transformed to result in rotation of the piston rod in a direction which in turn causes the piston rod to advance distally.*

*18. The injection mechanism of claim 17, wherein the dose dial drum rotates toward zero during injection as a result of an axial force being applied to an injection button.*

*19. An injection mechanism for driving a dose of medication from a cartridge in a syringe by transferring an axial force from a user to the cartridge, wherein the injection mechanism comprises:*

*a one piece rotatable piston rod having a first portion having a first thread having a first pitch and a second portion having a second thread having a second pitch that is different than the first pitch, wherein the first and second portions rotate together;*

*a first threaded element fixed with respect to an injection device housing, wherein the first threaded element engages the first thread of the piston rod; and*

*a tube that engages the second thread on the piston rod to form a not self-locking connection so that when the tube is moved axially toward the cartridge without rotating, the tube causes the piston rod to rotate and wherein the piston rod is displaced axially with respect to the housing as the first thread screws within the first threaded element during injection of the medication.*

*20. The injection mechanism of claim 19, further comprising a dose scale drum that is threadedly engaged with a second thread element that is fixed to the housing so that when an axial force is applied, the force induces rotational movement of the dose scale drum and wherein the tube may move axially without rotating while the dose scale drum is rotated.*

*21. The injection mechanism of claim 20, wherein the tube is prevented from rotating relative to the housing during injection of medication and wherein the dose scale rotates to a zero position during injection.*

*22. The injection mechanism of claim 21, wherein the dose scale drum is journalled on the tube.*

*23. The injection mechanism of claim 21, wherein tube is locked against rotations during an injection.*

*24. The injection mechanism of claim 20, further comprising a first button for setting a dose and a second button for receiving the force that is transferred to the cartridge from a user.*

*25. The injection mechanism of claim 22, wherein the piston rod has at least two different cross-sectional shapes.*

*26. The injection mechanism of claim 20, further comprising an injection button for being pressed during injection and for receiving the force necessary to drive the medication from the cartridge.*

*27. The injection mechanism of claim 24, wherein a user can reduce a wrongly set too large dose without injecting medication by merely rotating the first button in a direction opposite that which is used to set a dose.*

*28. The injection mechanism of claim 26, further comprising numbers disposed on the dose scale drum that are indicative of the size of a set dose and further comprising a window through which the numbers are viewed.*

*29. The injection mechanism of claim 27, wherein the dose scale drum is threadedly engaged with the second thread element via a non self-locking connection that allows the dose scale drum to rotate toward zero during injection and while the second button is pressed and while the tube is moved axially.*

*30. An injection mechanism for driving a dose of medication from a cartridge in a syringe, the injection mechanism comprising:*

*a rotatable one piece piston rod having first and second threaded sections that are distinct and have different pitches but wherein the first and second sections rotate and translate in unison;*

*a drive tube having a threaded interior portion for engaging the second thread on the piston rod;*

*wherein the piston rod is threadedly connected to a first threaded element that is rotationally and axially fixed with respect to a syringe;*

*wherein the tube engages the second piston rod thread and forms a non self-locking connection between the tube and the piston rod's second thread; and*

*wherein during injection the tube moves axially without rotating and thereby induces the piston rod to rotate which in turn causes the piston rod to advance axially by screwing through the first threaded element.*

*31. The mechanism of claim 30, wherein the mechanism further comprises a dose scale drum that rotates to a zero position during injection and wherein prior to injection the size of a set dose may be reduced without injecting medication by merely rotating the dose scale drum in a direction opposite that which is used to set a dose and wherein the dose scale drum's rotation to zero during injection is induced by an axial pressing force exerted by a user on an injection button during injection.*

*32. The mechanism of claim 31, wherein the dose scale drum rotates about the tube during injection of medication without being rotationally coupled to the tube during injection of medication.*

*33. The mechanism of claim 32, wherein the dose scale drum is threadedly engage with a second threaded element that is also rotationally and axially fixed.*

*34. An injection mechanism for injecting multiple doses of medication from a syringe, the mechanism comprising a rotating piston rod that, when it rotates, transmits a force to a cartridge containing medication, the force being large enough to expel medication from the cartridge, the piston rod comprising at least two different threaded sections having different threaded configurations and different pitches but wherein both sections are fixed together so that they rotate in unison.*

*35. The mechanism of claim 34, further comprising a scale drum having a numerical scale and a helical thread, wherein the numerical scale is visible to indicate a dose size that a user has set and wherein the mechanism expels a dose equal to that which is indicated on the scale during an injection.*

*36. The mechanism of claim 35, wherein the scale is visible in a window and wherein after a dose is set by rotating a dose setting member, the dose size may be reduced by mere rotation of the dose setting member in a direction opposite the dose setting direction without injecting medication.*

*37. The mechanism of claim 36, wherein the scale drum rotates toward a zero dose size during an injection as a result of its helical thread and wherein the piston rod rotates and moves in a distal direction during injection, wherein the rotation of the piston rod is induced by axially moving a tube element that is threadedly engaged with one thread on the piston rod and wherein the distal movement of the piston rod results from the other threaded element on the piston rod engaging a rotationally and axially fixed element.*

*38. An injection mechanism for a syringe comprising a cartridge of medication at one end, an injection button and dose setting button at the opposite end, wherein the injection mechanism comprises a piston rod having a first threaded portion with a first pitch and a second threaded portion with a second pitch, wherein the first and second portions are fixed together so that they rotate in unison, wherein the first threaded portion engages a complimentary first threaded element that is fixed with respect to the syringe and wherein the second threaded portion threadedly engages a tube having a portion having a thread complimentary to the second threaded portion of the piston rod, wherein when the tube moves axially, it induces the piston rod to rotate which in turn causes the piston rod to screw through the first threaded element and move axially.*

*39. The injection mechanism of claim 38, wherein the mechanism comprises a dose scale drum having dose size indicator numbers that are visible through a window in the housing and wherein the drum rotates to a zero position during injection and wherein the tube dose not rotate during injection.*

*40. The injection mechanism of claim 39, wherein the first section of the piston rod threadedly engages the first threaded*

*element, and wherein the first threaded element is fixed to the housing, thereby threadedly connecting the piston rod to the housing.*

*41. The injection mechanism of claim 40, wherein the threaded engagement between the second section of the piston rod and the tube is formed by a helical thread component on the second section of the piston rod engaging a complementary helical element inside the tube and wherein in a dose size is set by rotating a dose setting member in a first direction and wherein, if the dose size needs to be reduced after setting, merely rotating the dose setting member in an opposite direction will reduce the dose size without injecting medication from the syringe.*

*42. An injection device comprising:*

*a housing having a window,*

*a cartridge of medication,*

*a piston rod drive comprising:*

*a piston rod,*

*a first threaded section on the piston rod having a first thread,*

*a second and different threaded section on the piston rod having a different thread,*

*wherein the pitch of the second section is different from the pitch of the first section,*

*a tube, and*

*a dose drum,*

*wherein the first section of the piston rod is threadedly engaged with a first threaded element that is fixed to the housing,*

*wherein the dose drum is threadedly engaged with a second threaded element that is fixed to the housing,*

*wherein the tube is threadedly engaged with the second threaded section of the piston rod,*

*wherein during dose setting the tube rotates relative to the piston rod and moves axially relative to the piston rod,*

*wherein during injection the tube moves axially without rotating to induce rotation of the piston rod which causes the piston rod to screw through the first threaded element toward the cartridge,*

*wherein a dose is set by rotating a dose setting member in a first direction and wherein the size of the set dose may be reduced without injecting medication by merely rotating the dose setting member in a second, opposite direction,*

*wherein the dose drum rotates toward a zero position while a user exerts an axial dose injecting force on the device which drives the tube to move axially,*

*wherein the force is transferred to the cartridge from the user during injection to drive the medication from the cartridge, and*

*wherein the dose drum reaches the zero position upon completion of the injection.*

*43. The device of claim 42, further comprising a dose setting mechanism that comprises one-way coupling that prevents the piston rod from rotating in a direction that would cause it to screw away from the cartridge during injection.*

*44. The device of claim 42, further comprising a dose setting mechanism that prevents the piston rod from being rotating in a direction that would cause it to screw away from the cartridge when the tube is rotated relative to the piston rod to set a dose.*

*45. The device of claim 43, wherein the one-way coupling comprises a ratchet.*

*46. A medication delivery pen comprising:*

*a housing having proximal and distal ends and including a holder for containing a cartridge containing a medication to be delivered through a conduit connected to said cartridge;*

*a piston rod having a not circular cross-section and an outer thread;*

*a piston rod drive for driving said piston rod in a distal direction inside the cartridge, said piston rod drive including a first part rotatably mounted within said housing and mating with the not circular cross-section of said piston rod so that the piston rod rotates with the first part but the piston rod may move axially independent of the first part, and a second part integral with said housing and having an internal thread mating the thread of said piston rod to form a thread connection wherein rotation of said first part in a first direction relative to said second part drives the piston rod in a distal direction;*

*a one-way coupling between the first part of the piston rod drive and the housing, the coupling preventing said first part of said piston rod drive from rotating in a direction opposite to said first direction, and providing an initial reluctance that has to be overcome by a sufficiently strong rotational torque on said first part before said first part can rotate in the first direction; and*

*a dose setting mechanism comprising a not self locking thread connection along which an injection button by rotation of a dose setting element relative to the housing is screwed out from the proximal end of the housing and which thread connection by axially returning the injection button in a distal direction back into the housing transforms said axial movement to a rotational torque on the first part of the piston rod drive causing said first part to rotate in the first direction, provided that the rotational torque is strong enough to overcome the initial reluctance provided by the one-way coupling;*

*wherein a set dose may be reduced in size without having to axially pull apart any parts of the pen.*

*47. A medication delivery pen comprising:*

*a housing having proximal and distal ends and including a holder for containing a cartridge containing a medication to be delivered through a conduit connected to said cartridge;*

*a piston rod having a not circular cross-section and an outer thread;*

*a piston rod drive for driving said piston rod in a distal direction inside the cartridge, said piston rod drive including: a first part for imparting rotation to the piston rod but permitting the piston rod to move axially independent of the first part; and a second part integral with said housing and having an internal thread mating the thread of said piston rod to form a thread connection; wherein rotation of said piston rod, imparted by the first part, in a first direction relative to said second part, drives the piston rod axially in a distal direction;*

*a one-way coupling comprising:*

*a) an annular ring of equally spaced internal ratchet notches situated on the inside of said housing, which internal notches have a steep front edge and a ramp shaped trailing edge,*

*b) a pawl surrounding and rotationally linked to said piston rod and having at least a pair of resilient arms, each arm having a free end, and*

*c) means situated on said free end of each arm for engaging in the internal ratchet notches of said annular ring, which means engages in said internal*

*notches by (i) abutting said steep front edge of the internal notches, thereby preventing said pawl body and said piston rod from rotating in a direction opposite to said first direction, the prevented direction being one by which the piston rod would be transported in a proximal direction, and (ii) resting along the ramp shaped trailing edge of the internal notches, thereby providing an initial reluctance that has to be overcome by a sufficiently strong rotational torque before said pawl body and said piston rod can rotate in the first direction; and*

*a dose setting mechanism comprising a not self locking thread connection along which an injection button by rotation of a dose setting element relative to the housing is screwed out from the proximal end of the housing and which thread connection by axially returning the injection button in a distal direction back into the housing transforms said axial movement to a rotational torque on the piston rod and said pawl to rotate in a the first direction, provided that the rotational torque is strong enough to overcome the initial reluctance provided by the one-way coupling;*

*wherein a set dose may be reduced in size without having to axially pull apart any parts of the pen.*

*48. A medication delivery pen comprising:*

*a housing having proximal and distal ends and including a holder for containing a cartridge containing a medication to be delivered through a conduit connected to said cartridge;*

*a piston rod having a not circular cross-section and an outer thread;*

*a piston rod drive for driving said piston rod in a distal direction inside the cartridge, said piston rod drive including: a first part for imparting rotation to the piston rod but permitting the piston rod to move axially independent of the first part; and a second part integral with said housing and having an internal thread mating the thread of said piston rod to form a thread connection; wherein rotation of said piston rod, imparted by the first part, in a first direction relative to said second part, drives the piston rod axially in a distal direction;*

*a one-way coupling between the piston rod and the housing, the coupling preventing said the piston rod from rotating in a direction opposite to said first direction, and providing an initial reluctance that has to be overcome by a sufficiently strong rotational torque on the piston rod before the piston rod can rotate in the first direction; and*

*a dose setting mechanism comprising a not self locking thread connection along which an injection button by rotation of a dose setting element relative to the housing is screwed out from the proximal end of the housing and which thread connection by axially returning the injection button in a distal direction back into the housing transforms said axial movement to a rotational torque on the piston rod causing the piston rod to rotate in the first direction, provided that the rotational torque is strong enough to overcome the initial reluctance provided by the one-way coupling;*

*wherein a set dose may be reduced in size without having to axially pull apart any parts of the pen.*

* * * * *